United States Patent
Shalaby

(10) Patent No.: US 8,414,874 B2
(45) Date of Patent: Apr. 9, 2013

(54) MULTIFACETED ENDOVASCULAR STENT COATING FOR PREVENTING RESTENOSIS

(75) Inventor: Shalaby W Shalaby, Anderson, SC (US)

(73) Assignee: Poly-Med, Inc., Anderson, SC (US)

( * ) Notice: Subject to any disclaimer, the term of this patent is extended or adjusted under 35 U.S.C. 154(b) by 0 days.

(21) Appl. No.: 10/510,125

(22) PCT Filed: Apr. 23, 2003

(86) PCT No.: PCT/US03/12831
§ 371 (c)(1),
(2), (4) Date: Oct. 4, 2004

(87) PCT Pub. No.: WO03/090807
PCT Pub. Date: Nov. 6, 2003

(65) Prior Publication Data
US 2005/0158363 A1    Jul. 21, 2005

Related U.S. Application Data

(60) Provisional application No. 60/375,182, filed on Apr. 24, 2002.

(51) Int. Cl.
*A61K 31/74* (2006.01)
(52) U.S. Cl.
USPC ........................................ 424/78.17
(58) Field of Classification Search .............. None
See application file for complete search history.

(56) References Cited

U.S. PATENT DOCUMENTS

| | | |
|---|---|---|
| 3,755,558 A | 8/1973 | Scribner et al. |
| 3,773,919 A | 11/1973 | Boswell et al. |
| 5,073,381 A | 12/1991 | Ivan et al. |
| 5,149,747 A * | 9/1992 | Gersdorf et al. ............. 525/454 |
| 5,304,121 A * | 4/1994 | Sahatjian ...................... 604/509 |
| 5,654,381 A | 8/1997 | Hrkach et al. |
| 5,993,972 A | 11/1999 | Reich et al. |
| 6,124,256 A * | 9/2000 | Hayry et al. ...................... 514/2 |
| 6,210,717 B1 | 4/2001 | Choi et al. |
| 2001/0032014 A1 | 10/2001 | Yang et al. |
| 2002/0041893 A1* | 4/2002 | Ignatious et al. ............. 424/426 |
| 2002/0091433 A1* | 7/2002 | Ding et al. ..................... 623/1.2 |
| 2002/0164365 A1 | 11/2002 | Shalaby et al. |
| 2003/0083740 A1* | 5/2003 | Pathak ......................... 623/1.43 |

FOREIGN PATENT DOCUMENTS

| | | |
|---|---|---|
| EP | 0 737 703 A2 | 10/1996 |
| EP | 0 952 171 A2 | 10/1999 |
| WO | WO 99/21908 | 5/1999 |
| WO | WO 01/01890 | 1/2001 |
| WO | WO 02/055122 | 7/2002 |

OTHER PUBLICATIONS

Jarr E.M. et al, "Sustained release of lidocaine from an injectable implant system for treatment of post-operative pain," Proceedings of the International Symposium on Controlled Release of Bioactive Materials, vol. 26, Jul. 1999, pp. 631-632.

* cited by examiner

*Primary Examiner* — Paul Dickinson
(74) *Attorney, Agent, or Firm* — McCormick, Paulding & Huber LLP

(57) ABSTRACT

This invention deals with a carboxyl-bearing, amphiphilic, solid copolyester stent coating composition for multifaceted prevention of vascular restenosis through a plurality of physicopharmacological modes. The composition includes one or more bioactive compounds and a copolymerization product of polyalkylene glycol, end-grafted with one or more cyclic monomer and treated further to introduce carboxyl-bearing end- or side-groups. The invention also deals with bioactive agents in an ionically conjugated form. The present coating may be applied to a metallic or an absorbable polymeric stent for use in preventing vascular restenosis.

9 Claims, No Drawings

MULTIFACETED ENDOVASCULAR STENT COATING FOR PREVENTING RESTENOSIS

This application claims the benefit of prior provisional application, U.S. Ser. No. 60/375,182, filed Apr. 24, 2002.

FIELD OF THE INVENTION

This invention relates to biomedical applications of an amphiphilic, absorbable copolyester stent coating, which includes a bioactive agent to provide a multifaceted composition for preventing vascular restenosis through the simultaneous display of more than two of the key properties associated with rendering metallic and polymeric endovascular stents effective in preventing or minimizing restenosis.

BACKGROUND OF THE INVENTION

Cardiovascular and lumenal stents are highly effective in the treatment of heart disease and other vascular conditions by the dilation and retention of constricted vessels or bodily conduits. However, their insertion may induce undesirable bodily reactions such as inflammation, infections, thrombosis or blood clots, restenosis, and proliferation of cell growth that occludes the passageway and may incur the need for additional surgery. Pharmaceutical drugs and compounds may assist in preventing these conditions, although they may be required in large oral or intravenous doses with stringent intake or injection timetables to increase their efficacy.

Pharmaceutical compounds may be coated directly on the stent to provide a preferable point-of-use drug delivery system, but these coatings must be bioengineered to control the release of sometimes highly potent and potentially toxic drugs. Timed-release attributes of a coating must be incorporated to avoid clinically unacceptable premature releases of toxic levels of potent drugs. Biocompatible, biodegradable polymers for various biomedical applications such as those used in sutures and tissue engineering have been described in "Functionalized Polyester Graft Copolymers," Hrkach, et al., U.S. Pat. No. 5,654,381, issued Aug. 5, 1997. Drug-polymers based on polylactide and drug mixtures in particle or pellet form to provide timed-release delivery are described in "Polylactide-Drug Mixtures," Boswell, et al., U.S. Pat. No. 3,773,919, issued Nov. 20, 1973, or in a spray form as described in "Polylactide-Drug Mixtures for Topical Application," Scribner, et al., U.S. Pat. No. 3,755,558, issued Aug. 28, 1973.

These developments in pharmaceutical coatings, however, have limited control over the delivery of the drug and versatility in the types of drugs to be delivered and their pharmacodynamics. The delivery of the drug may be too fast, ineffective and possibly toxic, or too slow and ineffective. The drug coating may not stick or adhere. The drug polymer coatings should coat the stent framework without cracking, peeling or delaminating, particularly when the stent is expanded during installation. The coating should not fall off, crack, fracture, crystallize or melt during processing, sterilizing, or installing. In some cases, a rapid delivery of a drug may be needed immediately following surgery, followed by a steady delivery of the drug at a lesser rate over an extended period of time. Because there is need for the in vivo delivery of more than one drug, delivery of one or multiple drug types from a deployed, coated stent with variable elution rates is desirable. One drug type in a polymer coating may elute faster than another drug type in the same polymer, thus methods of modulating a drug without impacting its bioactive moiety are desirable.

In spite of the broad coverage of the prior art on the use endovascular stents for the prevention of restenosis entailing many types of stent polymeric barrier coatings and bioactive agents for inhibiting restenosis, integrating the role of both components into a physico-pharmacologically unique entity to maximize their efficacy as a physical barrier and pharmacologically active agent was left unaddressed. This and the availability of new forms of bioactive agents with more than one pharmacological effect provided an incentive to explore the concept of multifaceted coating composition subject of this invention.

SUMMARY OF THE INVENTION

Accordingly, the objective of this invention is to design a multifaceted coating composition, wherein the bioactive agent has more than one pharmacological attribute for preventing restenosis and also interacts with a functional polymeric barrier to modulate its bioavailability.

This and other goals are achieved by providing an absorbable, amphiphilic, solid copolyester stent coating composition for multifaceted prevention of vascular restenosis through a plurality of physicopharmacological modes, which includes at least one bioactive compound and a segmented/block copolymer having a central polyoxyalkylene segment and at least one terminal segment derived from at least one cyclic monomer, the copolymer having at least one carboxyl group per chain. Preferably, the polyoxyalkylene segment is polyoxyethylene and the chain has at least one carboxyl side group introduced by free-radically achieved maleation. Alternatively, the chain may include at least one carboxyl end group introduced by acylation of the at least one terminal segment with glutaric anhydride. In a preferred embodiment the at least one bioactive compound is a combination of two bioactive compounds such as an antiangiogenic compound and a non-steroidal anti-inflammatory drug, an antineoplastic agent and a non-steroidal anti-inflammatory drug, an antineoplastic agent and an anti-platelet aggregation drug, an antiangiogenic agent and anti-platelet aggregation drug, paclitaxel and a non-steroidal anti-inflammatory drug, or lanreotide and trapidil. For the latter embodiment it is preferred that the lanreotide is at least partially conjugated ionically with the segmented/block copolymer. In another embodiment the at least one bioactive compound is an ionic conjugate of a basic antiangiogenic peptide and an acidic non-steroidal anti-inflammatory drug. For such embodiment the acidic non-steroidal anti-inflammatory drug may be naproxen. The basic antiangiogenic peptide may be an LHRH analog or a somatostatin analog. In another embodiment the at least one bioactive compound is a combination of an antiangiogenic peptide, such as lanreotide, and an anti-platelet aggregation agent, such as trapidil, and the two are ionically conjugated with the segmented/block copolymer.

The present invention is also directed to a metallic endovascular stent coated with the present inventive absorbable stent coating. Further, the present invention is directed to an absorbable endovascular stent coated with the present inventive absorbable stent coating.

DESCRIPTION OF PREFERRED EMBODIMENTS

The primary objective of the present invention is to provide a coated, endovascular, metallic or polymeric stent comprising one or more bioactive agent that inhibits or minimizes the incidence of vascular restenosis. A preferred aspect of this invention deals with a metallic stent coated with a compliant, metal-adhering, absorbable copolyester that maximizes the mechanical biocompatibility of the metallic stent with the surrounding vascular tissues. Another preferred aspect of this invention deals with an absorbable amphiphilic copolyester coating on a metallic or polymeric endovascular stent with propensity for hydrophilic as well as hydrophobic bioactive agents. A specific aspect of this invention deals with a coating made by end-grafting a polyalkylene glycol and preferably polyethylene glycol with one or more of the following monomer, glycolide, trimethylene carbonate, lactide, ϵ-caprolactone, p-dioxanone, and 1,5-dioxepan-2-one that is further reacted with maleic anhydride in the presence of a free radical initiator to introduce anhydride side groups that can be converted to carboxylic groups. Another preferred aspect of this invention deals with a carboxyl-bearing, absorbable, amphiphilic copolyester capable of adhering to the surface of a metallic stent as well as ionic conjugation with basic bioactive agents. Another aspect of this invention deals with an absorbable, amphiphilic, carboxyl-bearing copolyester coating capable of (1) ionic conjugation with basic bioactive agents; and (2) adhering to an absorbable stent through chain interdiffusion at the stent/coating interface and/or acid-base interaction. Another preferred aspect of this invention deals with a coating comprising one or more bioactive agent that displays antiangiogenic, anti-inflammatory, and anti-neoplastic effects. A specific aspect of this invention describes the bioactive agent as a cyclic octapeptide. A more specific aspect of the invention describes the bioactive agent as cyclic octapeptide somatostatin analog such as those cited by Barrie et al., [*J. Surg. Res.*, 55, 446 (1993)] as the antiangiogenic peptide type, lanreotide. Another specific aspect of this invention describes the bioactive agent of a lutenizing human releasing hormone (LHRH) analog. A preferred aspect of this invention describes a basic somatostatin or LHRH analog as being present in part or fully as an ionic conjugate of a carboxyl-bearing anti-inflammatory drug such as naproxen. Another aspect of this invention deals with (1) a combination of an antineoplastic agent, such as paclitaxel or curcumin, and anti-inflammatory drug, such as naproxen; and (2) an antineoplastic agent, such as paclitaxel or curcumin, and an anti-platelet aggregation drug, such as trapidil. Another aspect of this invention deals with a mixture of bioactive agents comprising anti-angiogenic peptide such as one of the somatostatin analogs described above and a non-steroidal, anti-inflammatory drug (NSAID) such as naproxen. Another aspect of this invention deals with a mixture of bioactive agents comprising one of the somatostatin analogs described above and a second agent that is capable of mediating inflammation as well as inhibiting platelet aggregation such as trapidil. A specific aspect of this invention deals with a carboxyl-bearing amphiphilic copolyester stent coating, which is at least partially conjugated with a basic antiangiogenic peptide, such as lanreotide, and trapidil.

Another aspect of this invention deals with a non-absorbable, compliant, metal-adhering coating on an expandable metallic stent such as (1) butyl-methacrylate/methacrylic acid copolymer; and (2) vinyl-acetate butyl-methacrylate methacrylic acid terpolymer. A preferred aspect of this invention deals with one of the aforementioned types of non-absorbable coatings containing one or more of the bioactive agents described above in connection with the absorbable coating. A specific aspect of the non-absorbable coating deals with its use to bind at least part of a basic peptide, such as one of those noted above in the form of an ionic conjugate to control the release of such peptide.

Another aspect of this invention deals with the ionic conjugation of the carboxyl-bearing coating polymer with the basic peptide, which can be achieved by mixing an aqueous solution of an acetate salt of the peptide with a solution of the carboxyl-bearing polymer in a water-soluble solvent such as acetonitrile followed by separation of the precipitated polymer/peptide ionic conjugate. Alternatively, the peptide solution is allowed to react with an alkali metal salt of the carboxyl-bearing polymer to yield a precipitate of the polymer-peptide ionic conjugate.

Another aspect of this invention deals with a method of applying a solution of the coating on to a metallic or absorbable polymeric stent using any of the conventional methods, such as spraying, dipping, and ultrasonic atomization of a polymer solution comprising the bioactive agent or agents, followed by solvent removal by drying.

Additional illustrations of the present invention are given in the Examples discussed below:

EXAMPLE 1

Preparation of an Absorbable, Amphiphilic Copolyesters with Carboxy-Bearing Side-Groups: General Method In the first step, a predried polyethylene glycol is end-grafted with one or more cyclic monomer (e.g., ϵ-caprolactone, trimethylene carbonate, 1-lactide, glycolide, 1,5-dioxepan, and p-dioxanone) by a ring-opening mechanism, using a catalytic amount of stannous octoate at 150-60° C. for the proper period of time until practically a complete conversion of the monomer(s) is achieved (as determined by GPC). The resulting amphiphilic polymer is characterized for identity (IR and NMR), thermal properties (DSC), and molecular weight (GPC). In the second step, a solution of the amphiphilic polymer in a suitable solvent (e.g., toluene, dioxane) is reacted with maleic anhydride in the presence of a free-radical initiator (e.g., benzoyl peroxide, azo-bis-butyronitrile) at a suitable temperature (65-80° C.) for an appropriate period of time. The third step entails the treatment of the maleated product from Step 1 with water at 50° C. for 8-16 hours or until complete conversion of the anhydride side-groups to carboxylic groups (as determined by IR). The carboxyl-bearing polymer is then separated in a series of steps consisting of solvent evaporation under reduced pressure, rinsing with water, and centrifugation. The resulting product is characterized for identity (IR, NMR), thermal properties (DSC), molecular weight (GPC), and carboxyl content (acidimetry).

EXAMPLE 2

Preparation of Absorbable Amphiphilic Copolyester Based on Eng-Grafted Polyethylene Glycol (PEG) and Carboxyl-Bearing Side-Groups Using the general procedure of Example 1, PEG-5000, PEG 8000, and PEG-10,000 are converted to three different amphiphilic copolyesters (AMP-S1 to AMP-S3) as outlined in Table I. Hydrolysis of the anhydride group is conducted as in Example 1. The polymers are characterized for their identity, molecular weight, and thermal properties as discussed in Example 1.

TABLE I

Preparation of AMP-S1 to AMP-S3

| | Copolymer Number | | |
|---|---|---|---|
| | AMP-S1 | AMP-S2 | AMP-S3 |
| PEG Used, Average Molecular Weight, Da | 4600 | 8000 | 10,000 |
| End-grafting polymerization charge[a] | | | |
| PEG, moles | 0.02 | 0.016 | 0.001 |
| ε-Caprolactone, moles | 1.8 | 1.8 | 1.8 |
| 1-Lactide, moles | 0.2 | 0.2 | 0.2 |
| Stannous octoate, mmole | 0.2 | 0.2 | 0.2 |
| Maleation Reaction[b] | | | |
| Maleic anhydride, moles | 0.06 | 0.048 | 0.003 |
| Azo-catalyst, g | 1.5 | 1.5 | 1.5 |

[a]All reactions are conducted at 150° C. for 16–20 hours, or until complete monomer conversion.
[b]All reactions are conducted at 65° C. for 2–4 hours or until completion (as determined by IR).

EXAMPLE 3

Preparation of Carboxyl-Terminated, Absorbable Amphiphilic Copolyester—General Method This entails two steps. In the first step, a predried polyethylene glycol is end-grafted with one or more cyclic monomer (e.g., ε-caprolactone, trimethylene carbonate, 1-lactide, glycolide, 1,5-dioxepan, and p-dioxanone) by a ring-opening mechanism, using a catalytic amount of stannous octoate at 150-60° C. for the proper period of time until practically a complete conversion of the monomer(s) is achieved (as determined by GPC). The resulting amphiphilic polymer is characterized for identity (IR and NMR), thermal properties (DSC), and molecular weight (GPC). The second step entails the reaction of the end-grafted copolymer from Step 1 with a stoichiometric amount of glutaric anhydride at 140 to 160° C. for 3-4 hours or until end-group acylation is practically completed. The resulting polymer is characterized for identity (IR, NMR), thermal properties (DSC), molecular weight (GPC), and carboxylic content (acidimetry).

EXAMPLE 4

Preparation of Carboxyl-Terminated Absorbable Copolyester of Different PEGs

Using the general method of Example 3, PEG-2000, PEG-3000 and PEG-5000 are converted into three amphiphilic copolyesters (AMP-T1 to AMP-T3) as outlined in Table II. The carboxyl-terminated copolyesters are characterized as described in Example 3.

TABLE II

Preparation of AMP-T1 to AMP-T3

| | Copolymer Number | | |
|---|---|---|---|
| | AMP-T1 | AMP-T2 | AMP-T3 |
| PEG Used, Average Molecular Weight, Da | 2000 | 3400 | 4600 |
| End-grafting polymerization charge[a] | | | |
| PEG, moles | 0.05 | 0.025 | 0.02 |
| Caprolactone, moles | 1.8 | 1.8 | 1.8 |
| 1-Lactide, moles | 0.2 | 0.2 | 0.2 |
| Stannous octoate, mmole | 0.2 | 0.2 | 0.2 |
| Maleation Reaction[b] | | | |
| Maleic anhydride, moles | 0.1 | 0.05 | 0.04 |

[a]All reactions are conducted at 150° C. for 16–20 hours or until complete monomer conversion.
[b]All reactions are conducted at 65° C. for 2–4 hours or until complete consumption of the anhydride is realized (as determined by IR).

EXAMPLE 5

Preparation of Bioactive AMP-S1 Formulation with Lanreotide and Trapidil Hydrochloride and Stent Coating Therewith This entails two steps. In the first step, AMP-S 12 (1 g) from Example 2 is dissolved in acetonitrile (10 mL) and neutralized with aqueous sodium bicarbonate. To this is added, while stirring, a solution of lanreotide acetate (0.1 g) in water (0.5 mL) and mixing is continued for 1 hour at 25° C. to complete the formation of the AMP-S—lanreotide ionic conjugate. The latter was lyophilized to rid of the liquid components. The solid ionic conjugate is then redissolved in methylene chloride (10 mL) and a finely divided trapidil hydrochloride (0.1 g) is added while stirring. The solution of the bioactive formulation is filter-sterilized. The sterilized solution can then be applied to the metallic stent (or absorbable stent using non-solvent for stent upon preparing the sterile solution) by standard techniques (ultrasonic spraying, dipping). The coated stent is dried in a laminar flow hood prior to packaging.

EXAMPLE 6

Preparation of a Bioactive AMP-T1 with Lanreotide and Trapidil and Stent Coating Therewith This is pursued under similar conditions to those described in Example 5 with the exception of substituting AMP-T1 for AMP-S1.

EXAMPLE 7

Preparation of Bioactive AMP-S1 Ionically Conjugated with Lanreotide and Trapidil AMP-S1 (1 g) from Example 2 is dissolved in acetonitrile (10 mL) and neutralized with aqueous sodium bicarbonate. To this is added, while stirring, a solution of lanreotide acetate (0.08 g) in water (0.5 mL) followed by a solution of trapidil hydrochloride (0.002 g) in water (0.2 mL). Mixing is continued for 1 hour at 25° C. to complete the formulation of AMP-S1 ionic conjugate with lanreotide and trapidil. The reaction product is lyophilized to yield the solid conjugate.

EXAMPLE 8

Preparation of Ionic Conjugates of Lanreotide and Naproxen

A solution of lanreotide acetate (1 mmole, based on the active free base) in water (2.5 mL) is mixed with naproxen in the free acid form (1 mmole). The mixture of the two compounds is stirred at 25° C. under a nitrogen atmosphere until a clear solution is obtained. The latter is then lyophilized to produce a ready-to-use solid conjugate.

Although the present invention has been described in connection with the preferred embodiments, it is to be understood that modifications and variations may be utilized without departing from the principles and scope of the invention, as those skilled in the art will readily understand. Accordingly, such modifications may be practiced within the scope of the following claims. Moreover, Applicants hereby disclose all sub-ranges of all ranges disclosed herein. These sub-ranges are also useful in carrying out the present invention.

What is claimed is:

1. An absorbable, amphiphilic, solid copolyester stent coating composition for multifaceted prevention of vascular restenosis through a plurality of physicopharmacological modes comprising: 1) a side group carboxyl-bearing segmented/block copolymer comprising a central polyoxyalkylene segment and at least one terminal segment obtained by the ring-opening polymerization of at least one cyclic monomer, and 2) at least two bioactive compounds selected from antineoplastic drugs, non-steroidal, anti-inflammatory drugs, and antiplatelet aggregation drugs, at least one of said bioactive compounds being at least partially ionically conjugated to side carboxyl groups of said block copolymer.

2. An absorbable stent coating as set forth in claim 1 wherein the two bioactive compounds comprises an antineoplastic agent and a non-steroidal anti-inflammatory drug.

3. An absorbable stent coating as set forth in claim 1 wherein the at least one bioactive compound comprises an antineoplastic agent and an anti-platelet aggregation drug.

4. An absorbable stent coating as set forth in claim 1 wherein the at least one bioactive compound comprises an antiangiogenic agent and anti-platelet aggregation drug.

5. An absorbable stent coating as set forth in claim 1 wherein the two bioactive compounds comprise paclitaxel and a non-steroidal anti-inflammatory drug.

6. An absorbable stent coating as set forth in claim 1 wherein the non-steroidal anti-inflammatory drug comprises naproxen.

7. A metallic endovascular stent coated with the absorbable stent coating of claim 1.

8. An absorbable endovascular stent coated with the absorbable stent coating of claim 1.

9. An absorbable, amphiphilic, solid copolyester stent coating composition for multifaceted prevention of vascular restenosis through a plurality of physicopharmacological modes comprising: 1) a side group carboxyl-bearing segmented/block copolymer comprising a central polyoxyalkylene segment and at least one terminal segment obtained by the ring-opening polymerization of at least one cyclic monomer, and 2) at least two bioactive compounds selected from antineoplastic drugs, non-steroidal, anti-inflammatory drugs, and antiplatelet aggregation drugs, at least one of said drugs being at least partially ionically conjugated to side carboxyl groups of said block copolymer;
   wherein the coating provides for the sustained release of the two pharmacologically different bioactive compounds.

* * * * *